Figure 1:
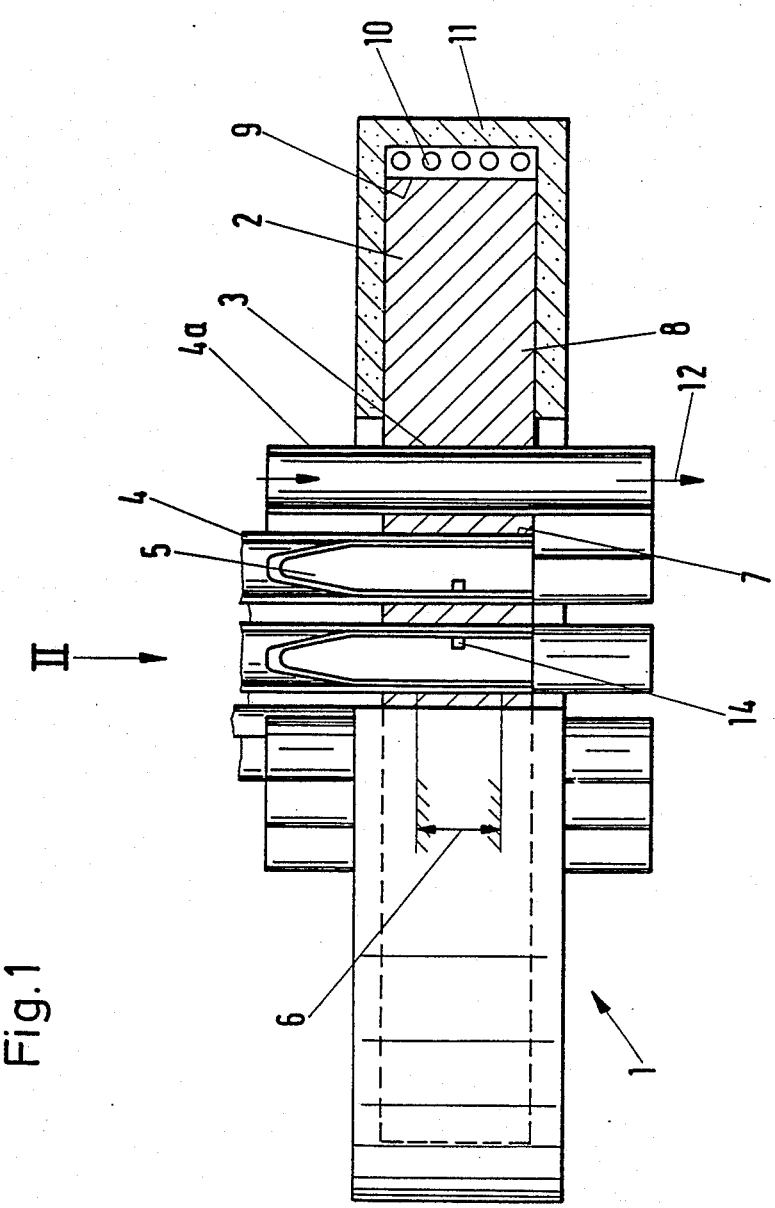

United States Patent [19]

Daum

[11] Patent Number: 4,822,176

[45] Date of Patent: Apr. 18, 1989

[54] METHOD AND APPARATUS FOR SIMULATION OF THE OPERATIONAL DEMANDS ACTING ON EXPANDED TUBE JOINTS

[75] Inventor: Dieter Daum, Heppenheim, Fed. Rep. of Germany

[73] Assignee: Brown Boveri Reaktor GmbH, Mannheim, Fed. Rep. of Germany

[21] Appl. No.: 192,954

[22] Filed: May 12, 1988

[30] Foreign Application Priority Data

May 21, 1987 [DE] Fed. Rep. of Germany ....... 3717032

[51] Int. Cl.[4] ............................................... G01N 3/06
[52] U.S. Cl. ........................................ 374/57; 374/45;
  374/55; 148/127; 73/865.6
[58] Field of Search ......................... 374/45, 46, 50, 55,
  374/56, 134, 4, 5, 43, 57; 73/760, 865.6, 866.4;
  148/127

[56] References Cited

U.S. PATENT DOCUMENTS

| | | | |
|---|---|---|---|
| 4,575,257 | 3/1986 | Ogura et al. ........................... | 374/45 |
| 4,592,662 | 6/1986 | Robins et al. .......................... | 374/55 |
| 4,772,336 | 9/1988 | Enomoto et al. ..................... | 148/127 |

Primary Examiner—William A. Cuchlinski, Jr.
Assistant Examiner—Diego F. F. Gutierrez
Attorney, Agent, or Firm—Herbert L. Lerner; Laurence A. Greenberg

[57] ABSTRACT

A method and apparatus for simulating operational demands acting on expanded tube joints includes penetrating a central inner region of a circular disc of a test body with a plurality of hollow cylinders. Sleeves or hollow plugs are connected to the hollow cylinders in the vicinity of the disc. A stress condition is created in the inner region corresponding to the operational demands by applying a force in an outer region of the disc through a uniform introduction of heat in the outer region while cooling the inner region. Outer hollow cylinders may serve as cooling passages and may form a boundary between the inner region and the outer region. Thermal insulation may be associated with the outer region. An electric resistance heater may be associated with the outer region for applying the force.

8 Claims, 2 Drawing Sheets

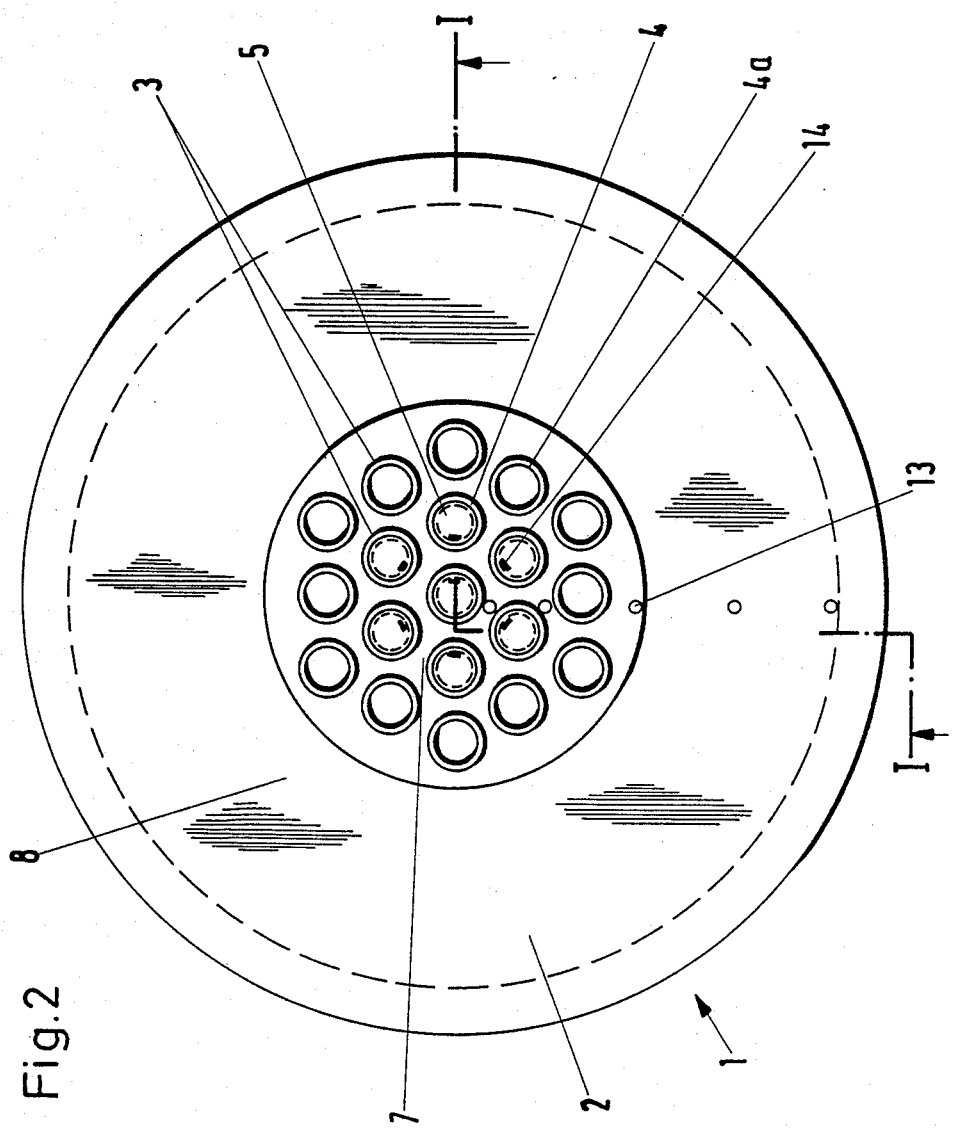

METHOD AND APPARATUS FOR SIMULATION OF THE OPERATIONAL DEMANDS ACTING ON EXPANDED TUBE JOINTS

The invention relates to a method for simulating operational demands acting on expanded tube joints, including a test body with a circular disc penetrated in a central inner region thereof by a plurality of hollow cylinders, sleeves or hollow plugs connected to the hollow cylinders in the region of the thickness of the disc, and a stress condition corresponding to the operational demands being created in the inner region by a force applied in the outer region of the test body.

In one method of this kind, the stress condition is produced by six hydraulic cylinders which are equally spaced around the circumference and which engage the peripheral surface, leading to a correspondingly large expense for technical equipment. In addition to the great expense for technical equipment, this method has the great disadvantage of causing the deformed condition of the test body to become too uneven, because the forces are only applied at six discrete points and not uniformly about the circumference.

It is accordingly an object of the invention to provide a method and apparatus for simulation of the operational demands acting on expanded tube joints, which overcomes the hereinafore-mentioned disadvantages of the heretofore-known devices of this general type and with which a uniform application of force from the periphery of the test body is accomplished in a simple manner.

With the foregoing and other objects in view there is provided, in accordance with the invention, a method for simulating operational demands acting on expanded tube joints, which comprises penetrating a central inner region of a circular disc of a test body with a plurality of hollow cylinders, connecting sleeves or hollow plugs to the hollow cylinders in the vicinity of the thickness of the disc, and creating a stress condition in the inner region corresponding to the operational demands by applying a force in an outer region of the disc through a uniform introduction of heat in the outer region while cooling the inner region.

The restriction on thermal expansion between the heated outer region and the cooled inner region of the disc produces a condition of tensile stress in the perforated inner region.

In accordance with another mode of the invention, there is provided a method which comprises adjusting the stress condition in the inner region by controlling at least one of the heating power or load or the cooling power or load.

In accordance with a further mode of the invention, there is provided a method which comprises monitoring tangential strain at locations where the hollow cylinders are connected to the hollow plugs or sleeves.

In accordance with an added mode of the invention, there is provided a method which comprises ascertaining the temperature of the disc at a plurality of locations.

With the objects of the invention in view, there is also provided an apparatus for simulating operational demands acting on expanded tube joints, comprising a test body including a circular disc having a central inner region and an outer region, a plurality of inner hollow cylinders penetrating the central inner region, sleeves or hollow plugs connected to the inner hollow cylinders in the vicinity of the thickness of the disc, outer hollow cylinders serving as cooling passages and forming a boundary between the inner region and the outer region, thermal insulation associated with the outer region, and an electric resistance heater associated with the outer region for applying a force in the outer region and creating a stress condition in the inner region corresponding to the operational demands.

In this way the heat of the outer region can be reliably delimited with respect to the inner region which is to be kept at a low temperature.

In accordance with an additional feature of the invention, the electric resistance heater is disposed on a peripheral surface of the outer region. This achieves a uniform entry or introduction of heat.

In accordance with still another feature of the invention, there is provided a strain gauge associated with an inner peripheral surface of one of the hollow plugs or sleeves in the vicinity the connection between the one hollow plug or sleeve and one of the inner hollow cylinders. This is done in order to ascertain the tangential strain.

In this way use is made of the fact that the tangential strain values measured on the interior of the hollow plug or the sleeve can be unambiguously converted into the corresponding strains in the contact zone between the hollow cylinder and the disc, or between the hollow cylinder and the hollow plug or sleeve, using the known stress/strain relationships.

In accordance with a concomitant feature of the invention, the strain gauge is disposed in the same given position with respect to holes formed in the disc for every simulation operation. This feature ensures reproducibility of the strain values in different simulation operations.

Other features which are considered as characteristic for the invention are set forth in the appended claims.

Although the invention is illustrated and described herein as embodied in a method and apparatus for simulation of the operational demands acting on expanded tube joints, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

FIG. 1 is a fragmentary, diagrammatic, half-sectional view of a test body for the simulation of the operating demands for a tube plate of a steam generator, taken along the line I—I in FIG. 2, in the direction of the arrows; and FIG. 2 is a plan view taken in the direction of an arrow II in FIG. 1.

Referring now to the figures of the drawings, there is seen a preferred embodiment of the invention in which a method and apparatus are used for simulation of operating demands which act on expanded joints made during steam generator repairs in the tube plate region during operation, testing and possibly during fault conditions. In such a case, defective steam generating tubes are commonly closed off by expansion of a hollow plug, or the damaged location is bridged by expansion of a sleeve. The connection between the sleeve or the hollow plug and the steam generator tube can also be produced by welding, soldering, adhesion or the like, in addition to expansion, shrinking or other resilient stressing. For example, the connection existing between a sleeve or a hollow plug and a steam generator tube must withstand at a temperature of more than 300° C., a primary-side pressure of 228 bar and a secondary-side pressure of 106, bar without leakage losses. During operation of the steam generator, this pressure difference leads to compressive or tension stresses on the lower surface of the tube plate of the steam generator, that is in the region of expansion of the hollow plugs or sleeves. According to experience, with the freshly expanded hollow plug or sleeve or steam generator tube, the tangential inherent compressive stresses introduced by the expansion lie only just below the yield point of the material. Therefore, compressive stresses in the tube plate and the associated increase of the compressive stresses in the plug produce a plastic deformation of the plug wall which manifests itself in plastic reverse upsetting or deformation of the expanded joint and also as a reduction of the total stressing after unloading.

With the method and the apparatus provided for carrying out the method described below, such loading situations are simulated in order to ensure the reliability of the connections during practical operation.

Referring now to the figures of the drawings in detail, there is seen a test body 1 formed of a circular disc 2, the center of which is penetrated by nineteen bores 3. A respective hollow cylinder 4 or 4a is expanded in each bore over the thickness of the disc, which amounts to about 50 mm. A respective hollow plug 5 with a predeterminable expansion region 6 is expanded in each of the seven inner hollow cylinders 4. The geometrical configuration of the bores 3, the dimensions of the hollow cylinders 4, 4a and of the hollow plugs 5, and the expansion technique, correspond to the requirements for expanded tube joints in the tube plate of steam generators that are to be simulated. The hollow cylinders 4, 4a are equated with the steam generator tubes. The seven hollow cylinders 4 fitted with hollow plugs 5 constitute an inner region 7 of the test body 1, which is separated from an outer region 8 of the test body 1 by the outer hollow cylinders 4a that are not fitted with hollow plugs. An electric resistance heater 10 is associated with a peripheral surface 9 of the disc 2, which is about 300 mm in diameter. The resistance heater and the remaining part of the outer region 8 are provided with insulation 11 for avoidance of heat losses.

In the method according to the invention, the outer region 8 is heated, while the inner region 7 is cooled by cooling water flowing through the outer hollow cylinders 4a (in the direction of an arrow 12). The incorporation of hollow cylinders 4a as cooling passages is not absolutely necessary. Instead, nonillustrated fittings can be screwed directly into the bores 3 and connected to a cooling water supply. The restriction on thermal expansion between the heated outer region 8 surrounded by the insulation 11 and the cooled inner region 7 of the disc 2, produces a condition of tensile stress in the perforated inner region 7, which can be finely matched to the desired loading conditions at the time, by regulating the heating. Depending on the stress condition to be simulated in the inner region 7, temperature differences up to about 300° C. appear between the inner region 7 and the outer region 8. The progress of these temperature differences is monitored by a plurality of temperature probes 13 disposed in the radial direction in the test body 1. The temporary production of a condition of tensile stress in the inner region 7 of the test body 1 results in an elastic enlargement of the bores 3 in the inner region 7, so that the above-mentioned permanent plastic reverse upsetting or deformation of the hollow plug 5 on the lower surface of the tube plate can be unambiguously simulated.

Since the hole geometry of the inner region 7 matches the actual tube plate of the steam generator, the distribution of stress and strain in the web or bridging region between the bores and especially the enhancement of stress and strain at the margins of the bores, is inevitably matched correctly.

In order to monitor the strain condition of the inner region 7, a respective strain gauge 14 is adhesively attached in the middle of the expanded region 6 in each hollow plug 5, as seen in the circumferential direction. The azimuthal position is chosen relative to an adjacent bore, with regard to reproducibility of the measured values. The tangential strain measurements which are ascertained at this easily accessible location can be unambiguously converted into corresponding strains in the contact zones, by using the known stress/strain relationships.

As soon as the corresponding desired value of the operational demand has been attained and held by the simulator, the tests necessary for approval of the expanded tube joint can be performed. Such tests are leak-resistance tests performed by helium leakage testing or hydraulic squeezing tests performed on the hollow plug. For the sake of simplification, the coupling connections and machines necessary for therefor are not shown, as is the case with the connections for the cooling water supply.

The foregoing is a description corresponding in substance to German Application P 37 17 032.5-52, dated May 21, 1987, the International priority of which is being claimed for the instant application, and which is hereby made part of this application. Any material discrepancies between the foregoing specification and the aforementioned corresponding German application are to be resolved in favor of the latter.

I claim:

1. Method for simulating operational demands on a connection between components, which comprises penetrating a central inner region of a circular disc of a test body with a plurality of hollow cylinders, connecting sleeves or hollow plugs to the hollow cylinders in the vicinity of the disc, and creating a stress condition in the inner region corresponding to the operational demands by applying a force in an outer region of the disc through a uniform introduction of heat in the outer region while cooling the inner region.

2. Method according to claim 1, which comprises adjusting the stress condition in the inner region by controlling at least one of heating power and cooling power.

3. Method according to claim 1, which comprises monitoring tangential strain at locations where the hollow cylinders are connected to the hollow plugs or sleeves.

4. Method according to claim 1, which comprises ascertaining the temperature of the disc at a plurality of locations.

5. Apparatus for simulating operational demands on a connection between components, comprising a test body including a circular disc having a central inner region and an outer region, a plurality of inner hollow cylinders penetrating said central inner region, sleeves or hollow plugs connected to said inner hollow cylinders in the vicinity of said disc, outer hollow cylinders serving as cooling passages and forming a boundary between said inner region and said outer region, thermal insulation associated with said outer region, and an electric resistance heater associated with said outer region for applying a force in said outer region and creating a stress condition in said inner region corresponding to the operational demands.

6. Apparatus according to claim 5, wherein said electric resistance heater is disposed on a peripheral surface of said outer region.

7. Apparatus according to claim 5, including a strain gauge associated with an inner peripheral surface of one of said hollow plugs or sleeves in the vicinity the connection between said one hollow plug or sleeve and one of said inner hollow cylinders.

8. Apparatus according to claim 7, wherein said strain gauge is disposed in the same given position with respect to holes formed in said disc for every simulation operation.

* * * * *